US006908439B2

(12) United States Patent
Carney (10) Patent No.: US 6,908,439 B2
(45) Date of Patent: Jun. 21, 2005

(54) CATHETER WITH DUAL TEMPERATURE DETECTION FOR VULNERABLE PLAQUE DETERMINATION

(75) Inventor: James Kevin Carney, Eden Prairie, MN (US)

(73) Assignee: Medtronic Vascular, Inc., Santa Rosa, CA (US)

(*) Notice: Subject to any disclaimer, the term of this patent is extended or adjusted under 35 U.S.C. 154(b) by 0 days.

(21) Appl. No.: 10/692,251

(22) Filed: Oct. 23, 2003

(65) Prior Publication Data

US 2005/0090761 A1 Apr. 28, 2005

(51) Int. Cl.[7] .................................................. A61B 5/00
(52) U.S. Cl. ...................................... 600/549; 600/585
(58) Field of Search ........................ 600/433–435, 600/549, 466, 505, 473, 474, 585, 264, 523; 374/100, 137

(56) References Cited

U.S. PATENT DOCUMENTS

| 3,595,079 | A | * | 7/1971 | Grahn ....................... 73/204.15 |
| 5,924,997 | A | * | 7/1999 | Campbell ..................... 600/549 |
| 2001/0053882 | A1 | * | 12/2001 | Haddock et al. ............. 600/549 |
| 2002/0082515 | A1 | * | 6/2002 | Campbell et al. ............ 600/549 |
| 2003/0120171 | A1 | * | 6/2003 | Diamantopoulos et al. . 600/549 |
| 2004/0073132 | A1 | * | 4/2004 | Maahs et al. ................. 600/549 |

* cited by examiner

Primary Examiner—Charles Marmor
Assistant Examiner—Sadaf Toor

(57) ABSTRACT

A method and system for determining vulnerable plaque in a cardiovascular lumen is disclosed. A guide member is inserted into the cardiovascular lumen. Temperature is sensed from a first position and a second position along the inserted guide member. Vulnerable plaque is determined based on the sensed temperature from the first position and the second position.

13 Claims, 6 Drawing Sheets

CATHETER WITH DUAL TEMPERATURE DETECTION FOR VULNERABLE PLAQUE DETERMINATION

FIELD OF THE INVENTION

This invention relates generally to the determination and location of vulnerable plaque. More specifically, the invention comprises a method and system for measuring fluid stream temperatures in pulsatory flow proximate the vulnerable plaque.

BACKGROUND OF THE INVENTION

Detection and stabilization or reduction of vulnerable plaque motivates the current research in vulnerable plaque diagnosis and treatment. The rupture of unstable or vulnerable atherosclerotic plaques located on the walls of coronary arteries, the carotid arteries, and other cardiovascular arteries, combined with associated thrombosis, is recognized as a common cause of acute coronary syndrome (ACS) such as unstable angina, myocardial infarction, and sudden ischemic cardiac death.

Vulnerable plaque is often formed in the vessels of the heart, vessels supplying blood to the brain, and other cardiovascular arteries. It largely goes undetected, though its shape and composition make it susceptible to disruption, resulting in blood clots that can cut the supply of blood to the heart or brain, producing chest pain, heart attack or stroke.

Vulnerable plaques are small lesions typically comprising a lipid-rich core, surrounded by a thin, collagenous cap with varying degrees of smooth muscle cells. The vulnerable plaques form within the walls of cardiovascular vessels, and are often eccentric in shape with irregular borders. The plaques may be characterized by a thickened arterial wall, partial stenosis, and generally elliptical distortion of the cardiovascular lumen with blockages ranging from zero up to about 70%. Stenoses are generally less severe with vulnerable plaques than stable plaques. However, mild stenoses are far more common and are responsible for more occlusions than tighter stenoses. Vulnerable plaques may be differentiated by their size, shape and composition of their lipid cores and fibrous caps. Acute lesions are larger with crescent-shaped cores rich in cholesterol esters with extracellular lipid accumulation. The fibrous cap may be infiltrated with macrophages throughout and at the borders in contact with normal intima, a precursor to initiating the disruption of the vulnerable plaque with mechanical strain or degradation of the wall thickness.

The fibrous cap may fatigue and rupture from mechanical stresses, releasing macrophages and tissue factor leading to thrombosis. Tension within the cap occurs with elevated blood pressure and larger vessel radius. Cyclical tension and compression of the cap occurs with normal systolic-diastolic pressure changes that increases with faster heart rate and increased activity. Bodily movements and physical exertion may stress the plaque and exacerbate the onset of fissures in the cap. The cap may also degrade from the secretion of proteolytic enzymes such as plasminogen activators and metalloproteinases from lipid-filled macrophages (foam cells) resulting in plaque disruption and atherogenic vulnerability. The cap may be compromised by the presence of inflammation and swelling. As a result, activated inflammatory cells release heat that, when detected, indicates the presence and progression of vulnerable plaque.

Many devices have been proposed to detect vulnerable plaque. Magnetic resonance imaging, nuclear imaging techniques, endovascular ultrasonography, angiography, angioscopy, infrared spectroscopy, and cardiovascular wall temperature measurements may be used to determine the presence and location of carotid, aortic and coronary atherosclerotic plaques. Included in such devices are thermal sensing catheters, as well as infrared and optical coherence tomography (OCT) catheters.

Vulnerable plaque differs from underlying tissue in that it typically has an elevated temperature. This elevated temperature, while distinct, may be difficult to detect due to the relatively small difference between the temperature of the fibrous cap and the normal vascular wall temperature. Measurement of temperature differences between vulnerable plaques and normal vessels provides direct evidence of inflammatory material in the plaque core and thin walls surrounding the core. Normal arterial wall temperatures are relatively constant, although patients with coronary artery disease of increasing severity have progressively larger temperature deviations between the plaque lesions and the baseline wall temperature. The temperature deviations range from less than 0.1 degrees centigrade for stable angina to above 1.5 degrees centigrade for acute myocardial infarction. Degradation of the cap thickness may further enhance the observable temperature differential, providing additional indications of severity and impending peril. Plaque rupture may be predicted by looking for hot spots in arterial walls that are caused by the release of heat from the activated inflammatory cells.

Invasive procedures may provide the best opportunity for vulnerable plaque identification and local treatment. Such methods are conveniently used during angioplasty or other surgical procedures when the patient is undergoing intensive procedures involving catheters.

Instrumented catheters provide imagery and sensor information as the guidewire and catheter body are manipulated through the larger arterial vessels in the body. Often catheters are inserted into the femoral artery in the thigh, and threaded up a circuitous path into the heart or through the carotid arteries and into the cerebellum. Cardiovascular wall temperatures may be extracted with thermocouple measurements from a suitably equipped guidewire. The thermocouple is tensioned with a graceful kink in the guidewire, providing direct contact with the lumen wall as the guidewire progresses through the vessels. Measurement accuracy is low due to the pulsing flow of blood in the vicinity of the thermocouple, which rapidly diffuses heat generated by the vulnerable plaque. Contact measurements present an intrinsic risk of generating fissures in the plaque wall and liberating its contents, while increasing the risk of thrombogenic responses and the potential for coronary failure.

Vulnerable plaque may be either simple, low-level lesions in an artery or may be protruding lesions in an artery. In a guidewire-based thermal sensing system, a thermal sensor is required to actually touch the vulnerable plaque lesion. When lesions protrude into the artery lumen, guidewire-based sensors may move past without touching and thus, the protruding lesions might not be detected.

Temperature measurements of the cardiovascular walls using intravascular, non-contact techniques are desirable to avoid undue traction with a vessel wall. Catheter-based apparatus may ascertain the presence and extent of vulnerable plaque, and allow for immediate, localized treatment of the atherosclerotic lesions. While non-contact, catheter-based diagnosis and treatment are attractive therapeutic methodologies for stabilization and abatement of vulnerable plaque, accurate determination of wall temperature is difficult due to the pulsating fluid flow through the vessel and around the temperature sensor. The amount of error in temperature measurement increases as a temperature sensor moves further from the vascular wall. Thermal imaging devices are similarly compromised due to varying opacities of the blood in the vessel. A measurement technique that allows accurate determination of cardiovascular wall temperature in the presence of pulsating flow within the blood vessel would be beneficial in providing an accurate assessment of the presence, severity and extent of any vulnerable plaque.

It is an object of this invention, therefore, to provide a method and system for determining vulnerable plaque and other vascular conditions using enhanced temperature-sensing techniques, to provide an option for local treatment or long term treatment of the vulnerable plaque, and to overcome the deficiencies and limitations described above.

SUMMARY OF THE INVENTION

A method of the current invention determines vulnerable plaque in a cardiovascular lumen. The method includes the steps of inserting an instrumented guidewire or catheter into the lumen, sensing temperature from a first position along the inserted guide member, sensing temperature from a second position along the inserted guide member near the first position, and determining the vulnerable plaque based on the sensed temperature from the first position and the second position.

Another aspect of the invention includes identifying placement of the temperature-sensing positions, and determining the location of the vulnerable plaque.

Another aspect of the invention comprises measuring the fluid flow in the lumen proximate the temperature-sensing positions, compensating the sensed temperatures based on the flow measurement, and determining the vulnerable plaque based on the difference between the compensated sensed temperatures.

Another aspect of the invention includes cooling bodily fluid flowing in the cardiovascular lumen to increase the temperature differential between the first position temperature and the second position temperatures.

Another aspect of the invention includes treating the vulnerable plaque.

A system and an apparatus for determining vulnerable plaque in a cardiovascular lumen are also disclosed.

The aforementioned, and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

The present invention is illustrated by the accompanying drawings of various embodiments and the detailed description given below. The drawings should not be taken to limit the invention to the specific embodiments, but are for explanation and understanding. The foregoing aspects and other attendant advantages of the present invention will become more readily appreciated by the detailed description taken in conjunction with the accompanying drawings, wherein.

DETAILED DESCRIPTION OF THE PRESENTLY PREFERRED EMBODIMENTS

One solution to the problem of vulnerable plaque detection is to use a two-sensor scheme on a guidewire or a catheter, whereby two sensors permit thermal detection downstream of a vulnerable plaque lesion and also sense temperature upstream of the lesion. Given that the vulnerable plaque lesion creates heat, the downstream sensor has a higher sensed temperature than the upstream sensor. The use of two sensors is especially useful because the blood exhibits a naturally occurring temperature wave on a beat-by-beat basis. In addition, a flow sensor may be used to dynamically set a threshold level for vulnerable plaque determination. Thus, the first upstream sensor may provide a baseline for calculating the temperature increase of a vulnerable plaque lesion as sensed by the downstream sensor.

Multiple temperature sensors along the axis and around the circumference of a guide wire or a catheter may be used to determine vulnerable plaque by measuring upstream and downstream temperatures in the bloodstream of a cardiovascular artery. Temperature sensors at various positions along the guide member may detect heat generated by inflammation within the vulnerable plaque cap or lipid core. Vulnerable plaque may be determined based on the sensed temperatures.

Another aspect of the present invention solves the problem of detection due to a small temperature difference between a vulnerable plaque lesion and otherwise healthy arterial walls by cooling blood in the region of the arteries so as to create a larger difference between the vulnerable plaque temperature and the underlying background temperature of the blood. Such cooling may be accomplished through the delivery of cold saline in the blood vessel, the use of a cold neck compress, or other techniques that cool the region of the cardiac arteries during the procedures of vulnerable plaque detection.

Figure 1:
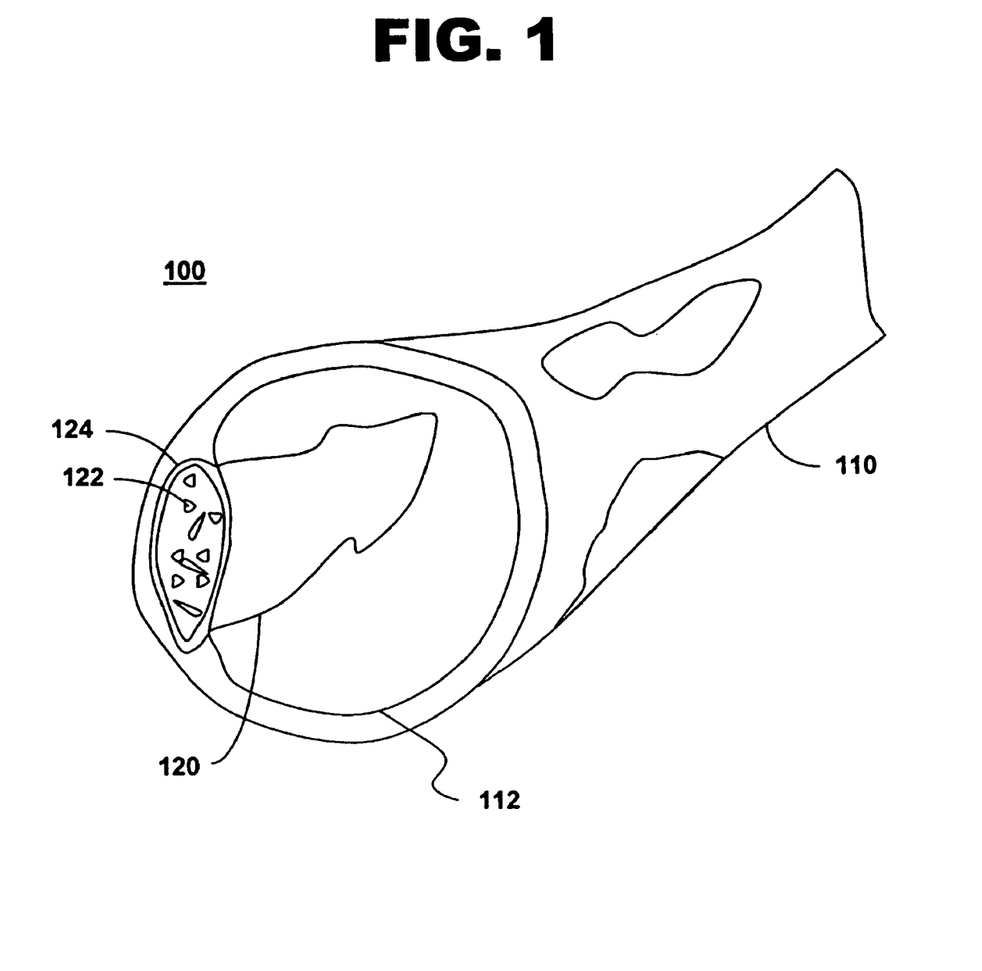
FIG. 1 is a pictorial illustration of a vulnerable plaque lesion lining the wall of a cardiovascular vessel.

FIG. 1 shows an illustration of a vulnerable plaque lesion lining the wall of a cardiovascular vessel at 100. A cardiovascular vessel 110, such as a vessel in the heart or leading to the brain, may be afflicted with vulnerable plaque 120. A soft, lipid core 122 surrounded by an irregular, fibrous cap 124 represents vulnerable plaque 120 within a cardiovascular wall 112. The vulnerable plaque may cause a partial stenosis of the blood vessel, producing local irregularities in the cross-sectional geometry of the artery.

Local heating of the blood occurs in the vicinity of the vulnerable plaque, the blood reaching a higher temperature when the blood flow is nearly stagnant and decreasing towards a baseline value when the blood flows rapidly through the region. At upstream and downstream locations away from the vulnerable plaque, the blood temperature tends towards a constant, uniform temperature. Near the vulnerable plaque, the temperature profile in the arterial vessel is highest at the cardiovascular wall, decreasing rapidly towards the center of the vessel and away from the lesion. The rate of blood flow and inflammation within the wall and core of the vulnerable plaque cause variations in the temporal and spatial temperature distributions depending on the severity of the vulnerable plaque and the proximity of the temperature sensors to the vulnerable plaque.

Figure 2:
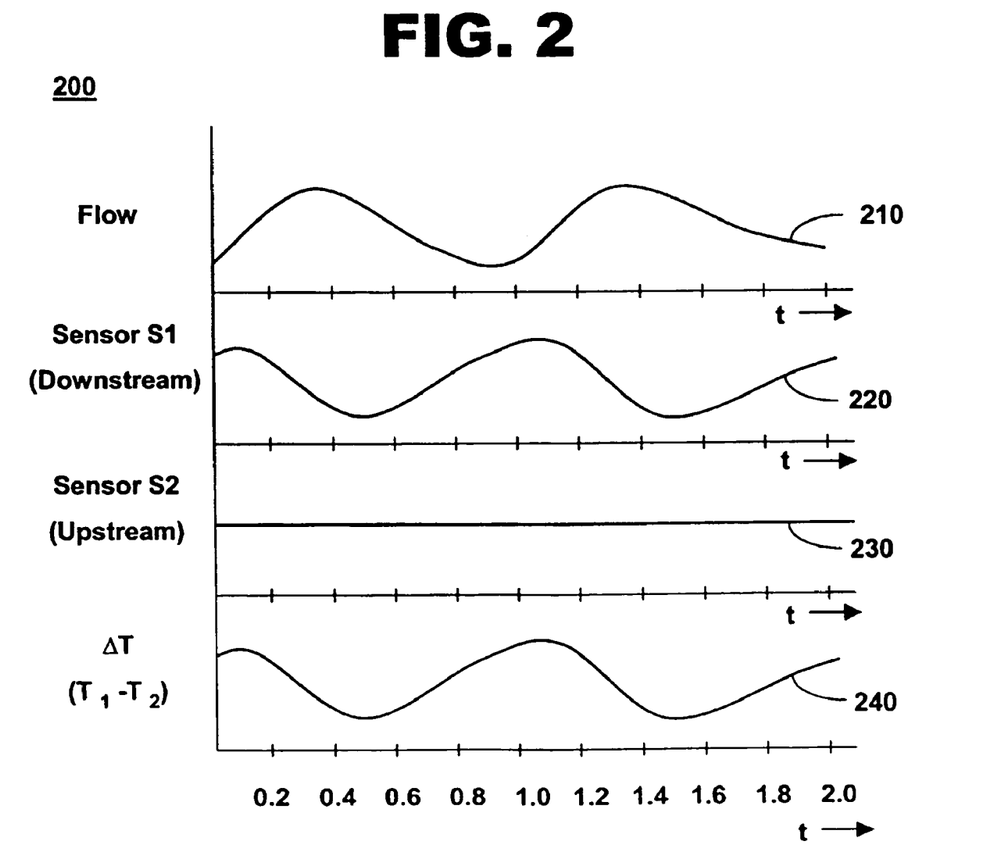
FIG. 2 is a graphical illustration of time-varying fluid flow and temperature at an instrumented guide member in a cardiovascular vessel, in accordance with the current invention.

FIG. 2 shows a graphical illustration of time-varying fluid flow and temperature at an instrumented guide member in a cardiovascular vessel, in accordance with the present invention at 200. Fluid flow and temperature variations change in a largely periodic manner with the pulsing of blood through the vessel. Blood flow profile 210 at some arbitrary point in the cardiovascular vessel is normally periodic and synchronized or partially delayed from the systolic-diastolic flow generated by the heart. The temperature of the blood is locally heated by vulnerable plaque on the vessel wall. A downstream temperature measurement taken close to the vulnerable plaque lesion would show a similarly pulsating nature, with highest temperatures reached after a time of nearly stagnant flow, and with lowest temperatures reached just after the occurrence of the highest blood flow, as shown by downstream temperature curve 220. Meanwhile, an upstream temperature sensor sufficiently away from the vulnerably plaque would show a nominally flat response, as shown by upstream temperature curve 230. The difference in the two responses will be dominated by the downstream temperature response, as indicated by the differential temperature curve 240.

Figure 3:
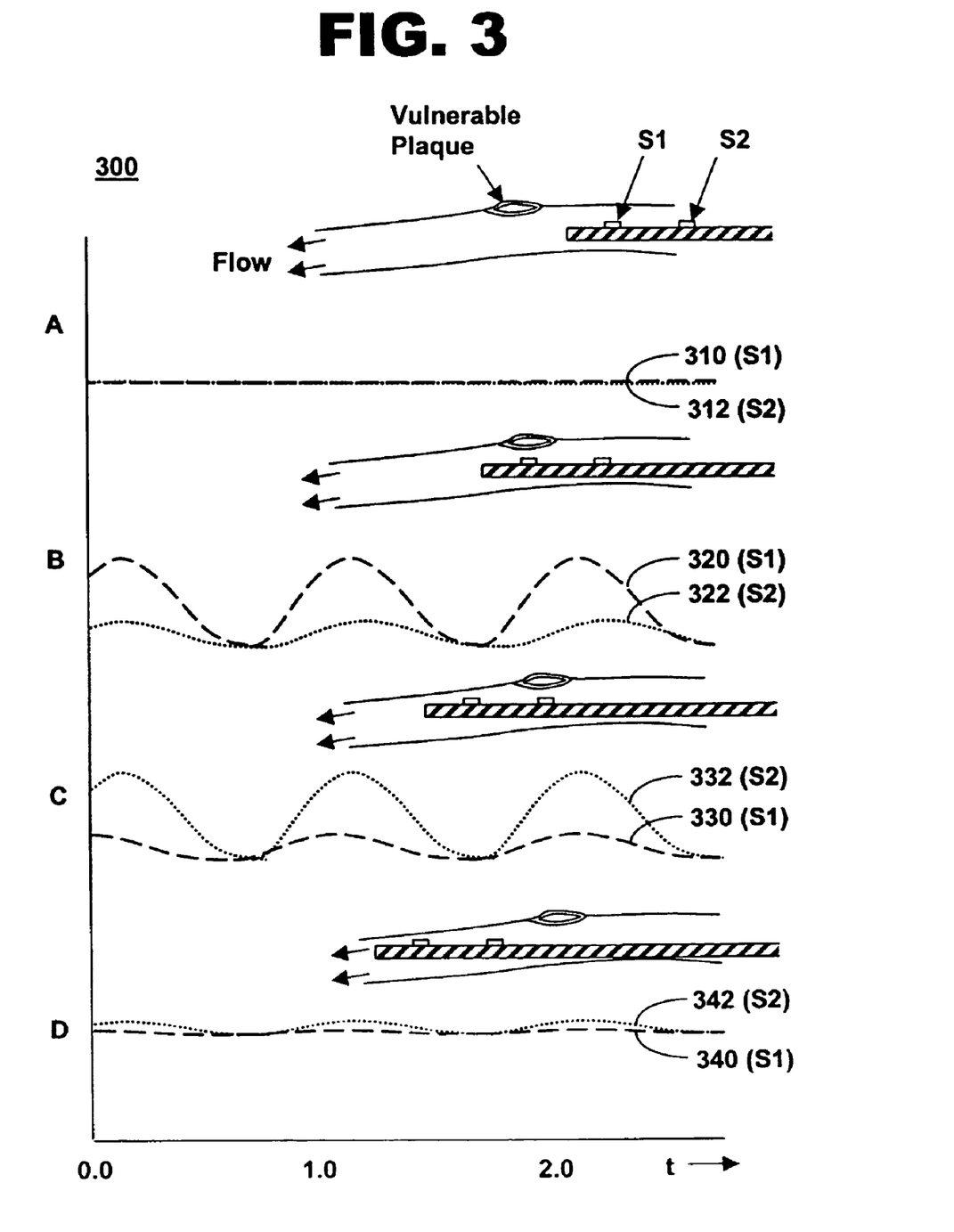
FIG. 3 is a graphical illustration of time-varying temperatures at an instrumented guide member in a cardiovascular vessel related to several exemplary temperature-sensing positions with respect to locations of vulnerable plaque on the vessel wall, in accordance with the current invention.

FIG. 3 shows a graphical illustration of time-varying temperatures at an instrumented guidewire or catheter in a cardiovascular vessel for several locations of temperature-sensing positions with respect to vulnerable plaque on the vessel wall, in accordance with the present invention at 300.

Periodically occurring fluid flow in the cardiovascular vessel creates periodic temperature variations in the vicinity of the vulnerable plaque. Approximately two cycles of the heartbeat are illustrated. Two temperature sensors axially located on a catheter or guidewire upstream of the vulnerable plaque result in nearly constant temperature profiles with time, as shown in case A by temperature signals 310 from temperature sensor S1 located at a first position and temperature signals 312 from temperature sensor S2 located at a second position along the guide wire. In case B, temperature sensor S1 is located proximal the vulnerable plaque, and temperature sensor S2 is located upstream from temperature sensor S1, providing temperature signals 320 from temperature sensor S1 and temperature signals 322 from temperature sensor S2. Temperature excursions are prominent from sensor S1, and less prominent with a minor phase delay from sensor S2. In case C, temperature sensor S1 is located downstream of the vulnerable plaque and temperature sensor S2 is located proximal the vulnerable plaque, providing temperature signals 330 from temperature sensor S1 and temperature signals 332 from temperature sensor S2. The resulting signals are highly prominent for temperature sensor S2, and noticeably less prominent for temperature sensor S1. In case D, both temperature sensors are well downstream of the vulnerable plaque, and temperature signals 340 from temperature sensor S1 and temperature signals 342 from temperature sensor S2 approach the baseline or background temperature.

Figure 4:
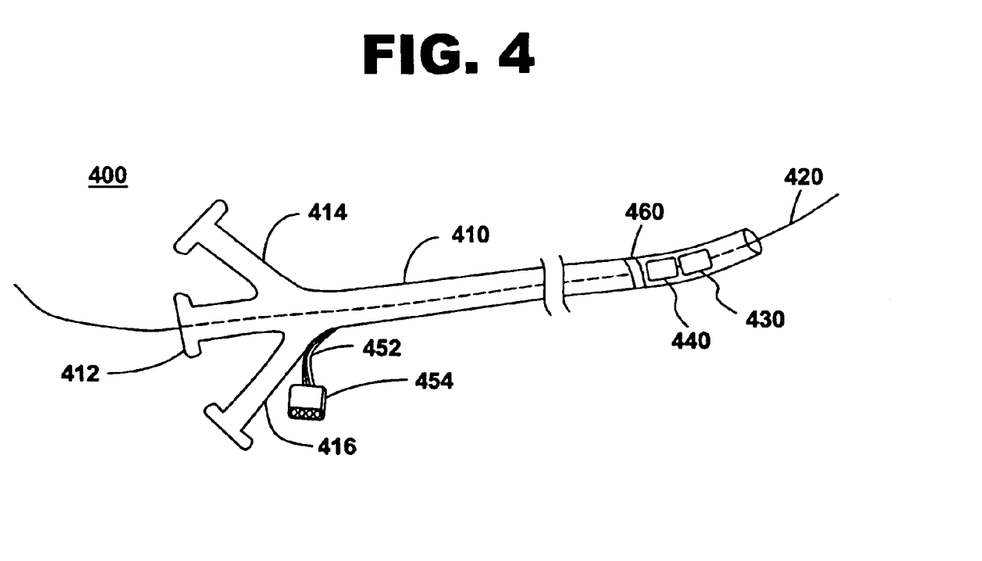
FIG. 4 is an illustration of a catheter instrumented with at least two temperature sensors, in accordance with the current invention.

FIG. 4 shows a catheter instrumented with at least two temperature sensors, in accordance with the present invention at 400. A catheter body 410 is typically a long, polymeric tube with a hollow interior, made from suitable biocompatible materials. The distal end of catheter body 410 has a hole for a guidewire 420. Guidewire 420 is typically of metallic construction that provides the required strength and flexibility without kinking or collapsing. Guidewire 420 may be inserted into the body first, through an incision into, for example, the femoral artery in the leg or groin region. Guidewire 420 may be maneuvered through various vessels in the body by careful pushing and twisting, while the progress may be observed on an external viewer of an imaging system. As the guidewire is maneuvered throughout the body, catheter body 410 may be slipped over guidewire 420 and guided along the vascular route. Guidewire 420 and catheter body 410 may be slid further into the body, until the guidewire and catheter are at their desired locations. The distal end of catheter body 410 may include a balloon for angioplasty, a stent, or other implantable or treatment device (not shown). The proximal end of catheter body 410 has a guidewire port 412 for loading, handling, and withdrawing guidewire 420. The proximal end of catheter body 410 may also have a pressure port 414 for enlarging a balloon or for deploying a stent at the end of catheter body 410. Pressure port 414 may be fluidically coupled to the distal end of catheter body 410 through an annular region within the catheter body for enlarging the balloon or deploying the stent. Catheter body 410 may also have a pressure relief port 416 for relieving pressure in the annular region of catheter body 410.

Near the distal end of catheter body 410 are at least two temperature sensors 430 and 440. Temperature sensor 430 and temperature sensor 440 may be mounted on the side of catheter body 410 or embedded in the polymeric casing. Temperature sensor 430 and temperature sensor 440 normally point outwards from catheter body 410 to observe the wall of the encroached vessel and to determine the temperature of the fluid in the vessel. Two or more temperature sensors may be positioned about the circumference of catheter body 410, or as desired along the length of catheter body 410. A first temperature-sensing device is operably attached to the guide member. A second temperature-sensing device spaced apart from the first temperature-sensing device is also attached to the guide member. The first and the second temperature-sensing devices may be located along the axis of the catheter or guidewire, in relatively close proximity so that changes between the temperature-sensing readings may be used to determine vulnerable plaque. Temperature-sensing devices in relatively close proximity may be separated, for example, by an amount on the order of the arterial diameter or on a characteristic length of the vulnerable plaque, for example, an average length of the unstable lesions. Multiple temperature sensors may give more temperature measurements for improved profiling of the vulnerable plaque along the length of the vessel. Multiple temperature-sensing devices may be included around the circumference of the guide member, providing circumferential information about the vulnerable plaque.

Temperature sensors 430 and 440 may be thermocouples, thermopiles, resistive temperature-sensing devices (RTD), or any suitable temperature-sensing devices for measuring elevated temperature areas of the intravascular fluid and the vessel wall. Temperature sensor 430 may comprise an infrared temperature detector such as a microbolometer for determining the vessel wall temperature. Due to the generally large absorption of infrared radiation by components in the blood, wall temperature measurements may use an infrared temperature detector with an optical passband corresponding to a region of transparency through bodily fluid within the cardiovascular lumen.

Electrical connections to the temperature sensors are made through catheter wiring 452 and a catheter connector 454. Catheter wiring 452 extends from each of the sensors back to the proximal end of catheter body 410. Catheter wiring 452 may consist of multiple stranded or solid core wires with electrical insulation. Catheter wiring 452 may line the outside of catheter body 410, the interior of catheter body 410, or be embedded within the polymeric tubing. Catheter wiring 452 may be connected to a catheter connector 454, which provides suitable strain relief and electrical coupling to external interface electronics.

Instrumented catheter body 410 may include a locator 460 for determining the position of the temperature sensor. Locator 460 may comprise a radiopaque marker. Radiopaque markers are relatively opaque to X-rays to produce an area of high contrast for external imaging. The radiopaque marker may be banded, bonded, or otherwise suitably attached onto catheter body 410. The radiopaque marker may comprise an inert, noble metal such as gold, platinum, iridium, palladium, rhodium, or other opaque, biocompatible material. An X-ray imaging system or other suitable imaging system may be used to determine the position of the marker and thereby determine the location of the temperature sensor and any detected vulnerable plaque.

Locator 460 may comprise a radio-frequency coil. The miniature coil may be mounted on or within the catheter body. Using external detection mechanisms and triangulation, the location of the coil and any vulnerable plaque may be determined. Locator 460 may comprise any suitable device for determining the location of the temperature sensing positions.

Figure 5:
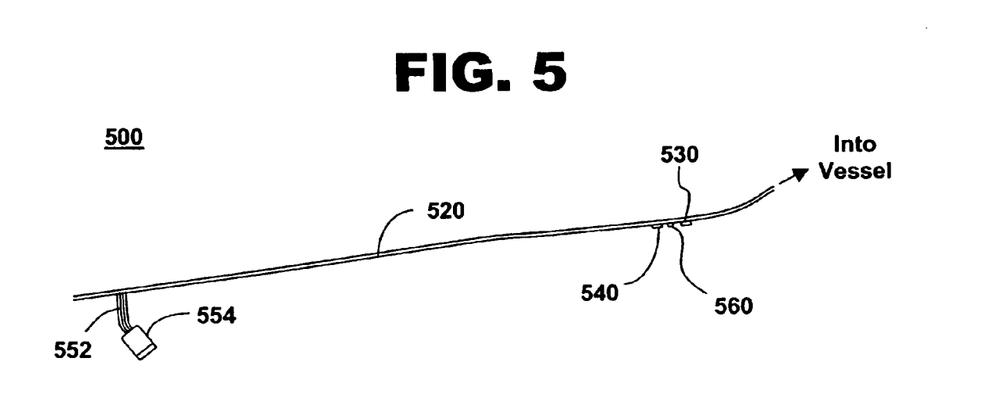
FIG. 5 is an illustration of a guidewire instrumented with at least two temperature sensors, in accordance with the current invention.

FIG. 5 shows a guidewire instrumented with at least two temperature sensors, in accordance with the present invention at 500. In this embodiment, two or more temperature sensors 530 and 540 are mounted onto the guidewire body 520. Temperature sensors 530 and 540 may be adhered to guidewire body 520 using a suitable epoxy or bonding technique and may be housed in one or more packages that are mounted to guidewire body 520.

An interconnect cable, such as thin, copper or metallic traces on a polyimide tape, may extend along guidewire body 520 and be used to connect temperature sensors 530 and 540 to guidewire wiring 552 and guidewire connector 554. Guidewire wiring 552 may comprise a ribbon cable or a bundle of insulated wires attached to guidewire body 520. Guidewire connector 554 provides suitable strain relief and electrical coupling to external interface electronics.

Instrumented guidewire body 520 may include a locator 560 for determining the position of the temperature sensors. Locator 560 may comprise a radiopaque marker, a radio-frequency coil, or other device for determining location. The radiopaque marker, comprising an inert, noble metal such as gold, platinum, iridium, palladium, rhodium, or other opaque, biocompatible material may be banded, bonded, or otherwise attached onto guidewire body 520. An X-ray imaging system or other suitable imaging system may be used to determine the position of the marker and thereby determine the location of any detected vulnerable plaque. Alternatively, locator 560 may comprise a radio-frequency coil. The miniature coil may be mounted on guidewire body 520. Using external detection mechanisms and triangulation, the location of the coil, the temperature-sensing positions, and any vulnerable plaque may be determined.

Figure 6:
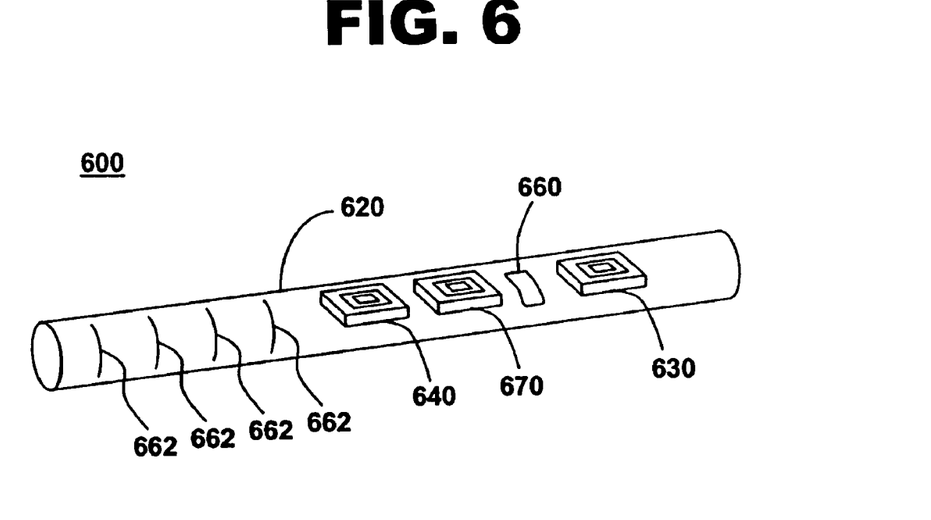
FIG. 6 is a perspective view of a portion of an indexed instrumented catheter or guidewire with a flow sensor and a location detector, in accordance with the current invention.

FIG. 6 shows a perspective view of a portion of an indexed instrumented catheter or guidewire with a flow sensor and a location detector, in accordance with the current invention at 600. Instrumented catheter or guidewire 600 includes a guide member 620 with a first temperature-sensing device 630 and a second temperature-sensing device 640. Guide member 620 may be a catheter or a guidewire. Temperature-sensing devices 630 and 640 are operably attached to guide member 620.

Guide member 620 may include a position locator 660 for determining the position of the temperature sensors. Position locator 660 may comprise a radiopaque marker, a radio-frequency coil, or other location determination device on the guide member.

Guide member 620 may include a series of marks 662 or other identifiers in a graduated manner to aid in identifying placement of the temperature-sensing positions and in determining the location of the vulnerable plaque. The indexed guide member 620 may have a series of circumferential marks 662 located at regular distances along the guide member, such that the user of the guide member can read the markings and determine how far in the guide member has been inserted into the body, thereby establishing the location of the vulnerable plaque.

Guide member 620 may include a flow sensor 670 located on or attached to the guide member proximate a first temperature-sensing device 630 and a second temperature-sensing device 640. Measurements of fluid flow along guide member 620 may be made by flow sensor 670 that is operably coupled to a controller and measures the flow of fluid within the cardiovascular lumen near the temperature-sensing positions. Measurements of fluid flow may be used to compensate the temperature sensor readings. Fast fluid flow rates may cause the downstream temperature sensor to read a higher value and the upstream temperature sensor to read a lower value, whereas slow fluid flow rates such as in a blocked artery or in an artery with significant stenosis either upstream or downstream of temperature sensors 630 and 640 may have less impact on the accuracy of the temperature sensor measurements. In normal pulsatory flow, compensation for the fluid flow may be needed for each temperature sensor reading. Indeed, the presence of a guidewire or catheter in the blood vessel can unduly exacerbate the flow rate in the vicinity of temperature sensors 630 and 640, possibly causing significant blockage, and thus measurements from them require compensation for the flow rate. Guide member 620 may be used to reduce the open cross-sectional area of the lumen, thereby increasing the flow through that region. Reducing the open cross-sectional area may help increase the velocity of the flowing blood, for example, by using a construction such as a gradated guide member 620.

Temperature measurements may be taken with an RTD, thermocouple, thermopile, infrared detector or any suitable temperature-sensing device or technique. Flow measurements may be made using any suitable flow sensor, such as a pressure-based flow sensor, an optical flow sensor, an ultrasonic flow sensor, a hot-wire anemometer sensor, or any appropriate flow-sensing device. Flow measurements may be used to adjust or compensate the temperature measurements for determining accurate lumen temperatures and for determining the vulnerable plaque based on the difference between the compensated sensed temperatures.

Figure 7:
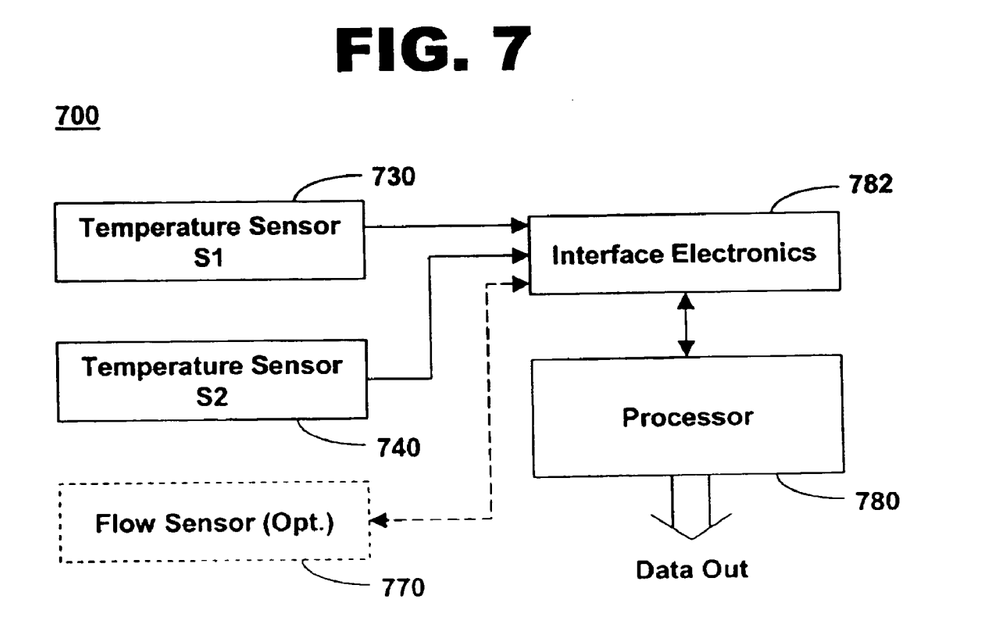
FIG. 7 is a block diagram of one embodiment of a system for determining vulnerable plaque in a cardiovascular lumen, in accordance with the current invention.

FIG. 7 shows a block diagram of one embodiment of a system for determining vulnerable plaque in a cardiovascular lumen, in accordance with the present invention at 700. Vulnerable plaque determination system 700 comprises two or more temperature sensors 730 and 740, digital signal controller or processor 780, and interface electronics 782. The temperature sensors are located on a guidewire or a catheter. An optional flow sensor 770 may be attached to or located on the guide member near the temperature-sensing devices. The instrumented guidewire or catheter is inserted into the body, and cardiovascular wall temperatures may be taken with temperature sensors 730 and 740 using interface electronics 782. Interface electronics 782 may include suitable amplifiers, signal conditioning circuits and analog-to-digital converters for biasing the temperature sensors and extracting a temperature measurement. Flow measurements may be taken with flow sensor 770 and interface electronics 782. Interface electronics 782 may also include suitable amplifiers, signal conditioning circuits and interface circuits for driving the flow sensor and extracting a flow measurement. The controller or processor 780 operably communicates with the first and second sensing devices, and determines a change between temperature sensor readings received from the first and second temperature-sensing devices. Using processor 780, the temperature measurements may be adjusted based on the flow determination, and vulnerable plaque may be determined based on the difference between the compensated sensed temperatures. Processor 780 may be a microcontroller, a microprocessor, a central processing unit (CPU), a host computer, a personal computer (PC), a networked computer, or any device capable of processing the measured data. Computer program code may provide instructions for processor 780 using any suitable programming language and any suitable computer readable medium.

Processor 780 may store multiple temperature and flow measurements as the instrumented guide member is moved throughout the vessel to determine a baseline temperature indicative of the background or normal temperature of the cardiovascular lumen. The baseline temperature may be established from multiple compensated sensed temperatures. Processor 780 may compare each compensated temperature measurement to the baseline temperature. Processor 780 may compute the difference between the compensated sensed temperatures and determine vulnerable plaque when the difference between the compensated sensed temperatures is greater than a predetermined threshold.

Figure 8:
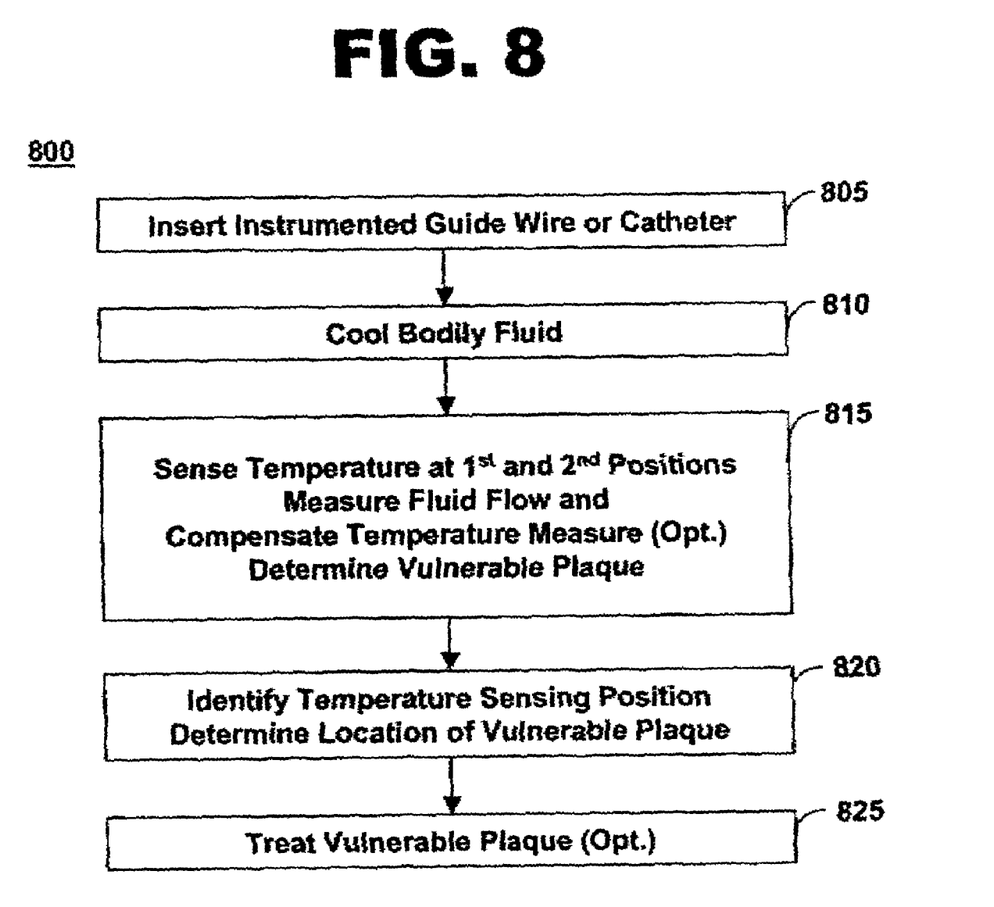
FIG. 8 is a flow diagram of one embodiment of a method for determining vulnerable plaque in a cardiovascular lumen, in accordance with the current invention.

FIG. 8 shows a flow diagram of one embodiment of a method for determining vulnerable plaque in a cardiovascular lumen, in accordance with the present invention at 800.

Vulnerable plaque determination method 800 begins by inserting an instrumented guide member such as an instrumented guidewire or an instrumented catheter into a cardiovascular lumen, as seen at block 805. The instrumented guidewire or catheter may include two or more temperature sensors operably coupled to the guide member. A first temperature sensor may be positioned on the guide member at a first position. A second temperature sensor may be positioned on the guide member at a second position spaced apart from the first position. The first and second temperature sensors may be located along the inserted guide member. Additional temperature sensors may be located about the circumference of the guide member. Other temperature sensors may be located along the length of the guide member. The temperature sensors may include one or more thermocouples, thermopiles, RTDs, infrared detectors, or any suitable temperature-sensing devices.

The instrumented guidewire or catheter may optionally include a flow sensor located on the guide member. The flow sensor may be used to measure flow of fluid within the cardiovascular lumen proximate the temperature-sensing positions. The flow sensor may be located on the guide member. The flow sensor may comprise a pressure-based flow sensor, an optical flow sensor, an ultrasonic flow sensor, a hot-wire anemometer flow sensor, or any suitable flow-sensing device.

Bodily fluid flowing in the cardiovascular lumen may be cooled to increase the change between the first position temperature and the second position temperature, as seen at block 810. Decreasing the temperature of the blood in the vessel provides a larger signal and therefore provides a higher signal-to-noise ratio and improves the accuracy of the method. Bodily fluid may be cooled, for example, by applying a cold compress on the neck of the patient. Alternatively, cold saline solution may be injected into the cardiovascular lumen or a patient may breathe cooled air to cool the bodily fluid. These and other techniques for cooling the bodily fluid help provide better temperature readings.

Temperature may be sensed from a first position along the inserted guide member, as seen at block 815. Temperature may be sensed from a second position along the inserted guide member near the first position. Vulnerable plaque may be determined based on the sensed temperature from the first position and the sensed temperature from the second position.

Optionally, the flow of fluid within the cardiovascular lumen near the temperature-sensing positions may be measured. The sensed temperatures from the first position and the second position may be compensated with the flow measurement. Vulnerable plaque may be determined based on the difference between the compensated sensed temperatures.

The placement of the temperature-sensing positions may be identified and the location of the vulnerable plaque determined, as seen at block 820. The temperature-sensing positions may be identified, for example, with an indexed guide member, a radiopaque marker on the guide member, or a radio-frequency coil on the guide member.

The vulnerable plaque may be treated, as seen at block 825. A determination may be made of vulnerable plaque on the vessel wall based on the sensed temperatures, and a local treatment may optionally be applied. The treatment may include immediate application of therapeutic drugs to the vulnerable plaque using, for example, a catheter-based drug delivery method on the instrumented guide member. Alternatively, the treatment may include determining the position of the vulnerable plaque, then removing the instrumented catheter or guidewire and replacing it with another catheter or guidewire that delivers therapeutic compounds.

A local therapeutic treatment may be immediately applied to vulnerable plaque when the instrumented catheter or guidewire is suitably equipped. In another embodiment of the present invention, the position of the vulnerable plaque is determined using one catheter or guidewire and another catheter is inserted to apply the treatment. In yet another embodiment of the present invention, the instrumented catheter or guidewire is removed, followed by a prescribed regimen of vulnerable plaque treatment medication such as statin therapy, which helps to stabilize or reduce the vulnerable plaque.

Although the present invention applies to the detection and treatment of vulnerable plaque, other cardiovascular and endovascular conditions may be accorded similar analysis and treatment.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for determining vulnerable plaque in a cardiovascular lumen, comprising:
   means for inserting a guide member into the cardiovascular lumen;
   means for sensing temperature from a first position along the inserted guide member;
   means for sensing temperature from a second position along the inserted guide member, the second position proximal the first position; and
   means for determining the vulnerable plaque based on the sensed temperature from the first position and the sensed temperature from the second position;
   means for compensating the sensed temperature from the first position with a flow measurement;
   means for compensating the sensed temperature from the second position with a flow measurement;
   means for determining the vulnerable plague based on the difference between the compensated sensed temperatures; and
   means for cooling bodily fluid flowing in the cardiovascular lumen to increase the change between the first position temperature and the second position temperature.

2. The system of claim 1 further comprising:
   means for identifying placement of the temperature-sensing positions; and
   means for determining a location of the vulnerable plaque.

3. The system of claim 1 further comprising:
   means for measuring flow of fluid within the cardiovascular lumen proximate the temperature-sensing positions.

4. The system of claim 1 further comprising:
   means for treating the vulnerable plaque.

5. A method for determining vulnerable plaque in a cardiovascular lumen, comprising:
   inserting a guide member into the cardiovascular lumen;
   sensing temperature from a first position along the inserted guide member;
   sensing temperature from a second position along the inserted guide member, the second position proximal the first position;
   determining the vulnerable plaque based on the sensed temperature from the first position and the sensed temperature from the second position; and
   cooling bodily fluid flowing in the cardiovascular lumen to increase the change between the first position temperature and the second position temperature.

6. The method of claim 5 wherein the first and second temperature-sensing positions comprise positions of temperature sensors located on the guide member.

7. The method of claim 5 further comprising:
   identifying placement of the temperature-sensing positions; and
   determining a location of the vulnerable plaque.

8. The method of claim 7 wherein the temperature-sensing positions are identified with one of an indexed guide member, a radiopaque marker on the guide member, or a radio-frequency coil on the guide member.

9. The method of claim 5 further comprising:
   measuring flow of fluid within the cardiovascular lumen proximate the temperature-sensing positions.

10. The method of claim 9 wherein the flow measurement uses a flow sensor located on the guide member.

11. The method of claim 9 further comprising:
    compensating the sensed temperature from the first position with the flow measurement;
    compensating the sensed temperature from the second position with the flow measurement; and
    determining the vulnerable plaque based on the difference between the compensated sensed temperatures.

12. The method of claim 5 wherein cooling bodily fluid comprises applying a cold compress on a neck, injecting a cold saline solution into the cardiovascular lumen, or breathing cooled air.

13. The method of claim 5 further comprising:
    treating the vulnerable plaque.

* * * * *

UNITED STATES PATENT AND TRADEMARK OFFICE
CERTIFICATE OF CORRECTION

| | | |
|---|---|---|
| PATENT NO. | : 6,908,439 B2 | Page 1 of 1 |
| APPLICATION NO. | : 10/692251 | |
| DATED | : June 21, 2005 | |
| INVENTOR(S) | : James Kevin Carney | |

It is certified that error appears in the above-identified patent and that said Letters Patent is hereby corrected as shown below:

Column 11, line 32, "vulnerable plague" should be changed to -- vulnerable plaque --

Signed and Sealed this

Second Day of January, 2007

JON W. DUDAS
*Director of the United States Patent and Trademark Office*